US012667319B2

(12) United States Patent
Turner et al.

(10) Patent No.: US 12,667,319 B2
(45) Date of Patent: *Jun. 30, 2026

(54) THREE DIMENSIONAL RADIATION IMAGE RECONSTRUCTION

(71) Applicant: TURNER INNOVATIONS, LLC, Orem, UT (US)

(72) Inventors: D. Clark Turner, Payson, UT (US); Douglas P. Hansen, Spanish Fork, UT (US); Thomas L. Youd, Holladay, UT (US); Michael P. Orthner, Bountiful, UT (US)

(73) Assignee: TURNER INNOVATIONS, LLC, Orem, UT (US)

( * ) Notice: Subject to any disclaimer, the term of this patent is extended or adjusted under 35 U.S.C. 154(b) by 377 days.

This patent is subject to a terminal disclaimer.

(21) Appl. No.: 18/179,599

(22) Filed: Mar. 7, 2023

(65) Prior Publication Data

US 2023/0240633 A1     Aug. 3, 2023

Related U.S. Application Data

(63) Continuation-in-part of application No. 17/052,137, filed as application No. PCT/US2019/018574 on Feb. 19, 2019, now Pat. No. 11,612,370.

(Continued)

(51) Int. Cl.
*A61B 6/00* (2024.01)
*A61B 6/46* (2024.01)

(52) U.S. Cl.
CPC ............ *A61B 6/466* (2013.01); *A61B 6/4405* (2013.01); *A61B 6/4441* (2013.01); *A61B 6/5211* (2013.01); *A61B 6/547* (2013.01)

(58) Field of Classification Search
CPC ...................................................... A61B 6/032
See application file for complete search history.

(56) References Cited

U.S. PATENT DOCUMENTS 7,333,588 B2    2/2008  Mistretta et al.
7,342,992 B2    3/2008  Schomberg
(Continued)

FOREIGN PATENT DOCUMENTS

JP      2004517670 A    6/2004
JP      2006055645 A    3/2006
WO      2016172611 A1   10/2016

OTHER PUBLICATIONS

JPO; App. No. 2020-543077; Office Action mailed Jan. 13, 2023.
(Continued)

*Primary Examiner* — Dani Fox
(74) *Attorney, Agent, or Firm* — Kenneth E. Horton; Barnes & Thornburg LLP

(57)         ABSTRACT

X-ray devices and systems are described in this application. In particular, this application describes x-ray devices and systems that are used for three-dimensional (3D) image reconstruction with uncertain geometry. The x-ray imaging system contains an arm configured to be moved around an object to be imaged, a light weight, low power x-ray source attached to the arm, an x-ray detector configured to move complimentary to the x-ray source to capture multiple two-dimensional (2D) images in a solid angle path outside of a planar arc, 3D position and orientation tracking device(s) configured to capture the geometric position and orientation of the x-ray source and detector when each 2D projection image is captured, and a processor configured to construct a three dimensional (3D) image from the multiple 2D images using a reconstruction algorithm. These x-ray systems are lighter, more maneuverable, and less expensive than conventional CT x-ray systems because the geometry (Continued)

tracking devices combined with the processor and algorithm enable the generation of 3D images without the complex, precise, heavy, and expensive mechanical system that fixes the precise geometry of each 2D projection image to a high degree of accuracy. Other embodiments are described.

21 Claims, 9 Drawing Sheets

Related U.S. Application Data

(60) Provisional application No. 62/631,569, filed on Feb. 16, 2018.

(56) References Cited

U.S. PATENT DOCUMENTS

| | | | | |
|---|---|---|---|---|
| 7,490,982 | B2 | 2/2009 | Gregerson et al. | |
| 9,014,328 | B2 | 4/2015 | Funk | |
| 9,442,083 | B2 | 9/2016 | Turner et al. | |
| 11,612,370 | B2 * | 3/2023 | Turner | A61B 6/027 |
| | | | | 378/98 |
| 2006/0039537 | A1 | 2/2006 | Strobel | |
| 2006/0118732 | A1 | 6/2006 | Blanton et al. | |
| 2007/0269001 | A1 | 11/2007 | Maschke | |
| 2008/0037701 | A1 | 2/2008 | Banks | |
| 2014/0031664 | A1 | 1/2014 | Kang et al. | |
| 2014/0049629 | A1 * | 2/2014 | Siewerdsen | A61B 34/20 |
| | | | | 348/77 |
| 2015/0196262 | A1 | 7/2015 | Grady | |
| 2015/0374319 | A1 | 12/2015 | Claus et al. | |
| 2016/0287197 | A1 | 10/2016 | Risher-Kelly | |
| 2018/0108447 | A1 | 4/2018 | Turner et al. | |
| 2020/0345318 | A1 | 11/2020 | Turner et al. | |

OTHER PUBLICATIONS

Rottman et al. "Joint Cone-Beam Reconstruction and Geometry Estimation for Mobile C-arms." In Fully Three-Dimensional Image Reconstruction in Radiology and Nuclear Medicine, pp. 697-700, 2015.

V. Y. Panin, G. L. Zeng, and G. T. Gullberg, "Total Variation Regulated EM Algorithm," IEEE Transactions on Nuclear Science, vol. 46, No. 6, pp. 2202-2210, 1999.

Donghwan Kim, Sathish Ramani, and Jeffrey A. Fessler. "Combining Ordered Subsets and Momentum for Accelerated X-ray CT Image Reconstruction." IEEE Transactions on Medical Imaging, 34(1):167-178, 2015.

http://www.analog.com/media/en/news-marketing-collateral/product-highlight/Tactical-Grade-IMU.PDF.

http://www.vectornav.com/.

http://www.chrobotics.com/library/accel-position-velocity.

Rottman et al. "Mobile C-arm 3D Reconstruction in the Presence of Uncertain Geometry" Scientic Computing and Imaging Institute, University of Utah, pp. 1-9.

A. Cheryauka, S. Breham, and W. Christensen, "Sequential Intrinsic and Extrinsic Geometry Calibration in Fluoro CT Imaging with a Mobile C-arm," in Proc. SPIE, vol. 6141, Mar. 2006, pp. 61412H-61412H8.

* cited by examiner

THREE DIMENSIONAL RADIATION IMAGE RECONSTRUCTION

CROSS-REFERENCE TO RELATED APPLICATIONS

This application is a continuation-in-part of U.S. application Ser. No. 17/052,137, filed on Oct. 30, 2020, which is a national stage application of PCT/US2019/018574, filed on Feb. 19, 2019, which claims priority of U.S. Provisional Application Ser. No. 62/631,569 filed on Feb. 16, 2018, the entire disclosures of which are incorporated herein by reference.

FIELD

This application relates generally to X-ray equipment. More specifically, this application relates to x-ray devices and systems that are used for three dimensional (3D) image reconstructions with uncertain geometry.

BACKGROUND

X-ray imaging systems typically contain an X-ray source and an X-ray detector. X-rays are emitted from the source and impinge on the X-ray detector to provide an X-ray projection image, or a shadow image, of the object or objects that are placed between the X-ray source and the detector. The X-ray detector is often an image intensifier or even a flat panel digital detector.

X-ray imaging systems have been developed that produce either 2D or 3D images. The imaging systems that produce 3D images typically employ computed tomography techniques to reconstruct a 3D image from multiple 2D images. These 3D X-ray systems are typically large and expensive, and deliver a higher radiation dose to the patient because of the numerous x-ray projection images required for the reconstruction calculations. They are used judiciously because of the expense and the inconvenience of obtaining a 3D image. Other concerns with such 3D imaging systems are the high radiation dose delivered to the patient. Thus, 3D imaging systems are not used in many instances where patients would benefit from the additional detail and insight that can be provided by 3D images if they were more readily available.

SUMMARY

This application relates generally to x-ray devices and systems. In particular, this application describes x-ray devices and systems that are used for three-dimensional (3D) image reconstruction with uncertain geometry. The x-ray imaging system contains an arm configured to be moved around an object to be imaged, a light weight, low power x-ray source attached to the arm, an x-ray detector configured to move complimentary to the x-ray source to capture multiple two-dimensional (2D) images in a solid angle path outside of a planar arc, 3D position and orientation tracking device(s) configured to capture the geometric position and orientation of the x-ray source and detector when each 2D projection image is captured, and a processor configured to construct a three dimensional (3D) image from the multiple 2D images using a reconstruction algorithm. These x-ray systems are lighter, more maneuverable, and less expensive than conventional CT x-ray systems because the geometry tracking devices combined with the processor and algorithm enable the generation of 3D images without the complex, precise, heavy, and expensive mechanical system that fixes the precise geometry of each 2D projection image to a high degree of accuracy.

BRIEF DESCRIPTION OF THE DRAWINGS

The following description can be better understood in light of the Figures which show various embodiments and configurations of the imaging systems and methods. Together with the following description, the Figures demonstrate and explain the principles of the structures, methods, and principles described herein. In the drawings, the thickness and size of components may be exaggerated or otherwise modified for clarity. The same reference numerals in different drawings represent the same element, and thus their descriptions will not be repeated. Furthermore, well-known structures, materials, or operations are not shown or described in detail to avoid obscuring aspects of the described devices.

DETAILED DESCRIPTION

The following description supplies specific details in order to provide a thorough understanding. Nevertheless, the skilled artisan will understand that the described X-ray systems can be implemented and used without employing these specific details. Indeed, the described systems and methods can be placed into practice by modifying the described systems and methods and can be used in conjunction with any other apparatus and/or techniques conventionally used in the industry. For example, while the description below focuses on imaging systems using x-rays, other forms of electromagnetic or atomic radiation could be used, including gamma rays, neutron radiation and infra-red or visible light, depending on the absorptive characteristics of the objects to be imaged by the desired radiation. Ultrasonic energy could also be used with the appropriate sources and detectors to generate 3D images in a similar manner. In another example, while the description below focuses on c-arms, other system configurations that hold the x-ray source and detector in a fixed position relative to one another while they are moved around the object during an imaging scan, such as O-arms, could be used successfully. It is even possible to move the x-ray source and detector independently around an object during an imaging scan as long as the 3D position of each is accurately recorded for each image, though this might complicate the image reconstruction process and may result in undesirable reconstruction artifacts in the 3D image, or perhaps require too much computing power and time to generate a 3D image in a useful time frame given current computer technology.

In addition, as the terms on, disposed on, attached to, connected to, or coupled to, etc. are used herein, one object (e.g., a material, element, structure, member, etc.) can be on, disposed on, attached to, connected to, or coupled to another object-regardless of whether the one object is directly on, attached, connected, or coupled to the other object or whether there are one or more intervening objects between the one object and the other object. Also, directions (e.g., on top of, below, above, top, bottom, side, up, down, under, over, upper, lower, lateral, orbital, horizontal, etc.), if provided, are relative and provided solely by way of example and for ease of illustration and discussion and not by way of limitation. Where reference is made to a list of elements (e.g., elements a, b, c), such reference is intended to include any one of the listed elements by itself, any combination of less than all of the listed elements, and/or a combination of all of the listed elements. Furthermore, as used herein, the terms a, an, and one may each be interchangeable with the terms at least one and one or more.

Figure 1:
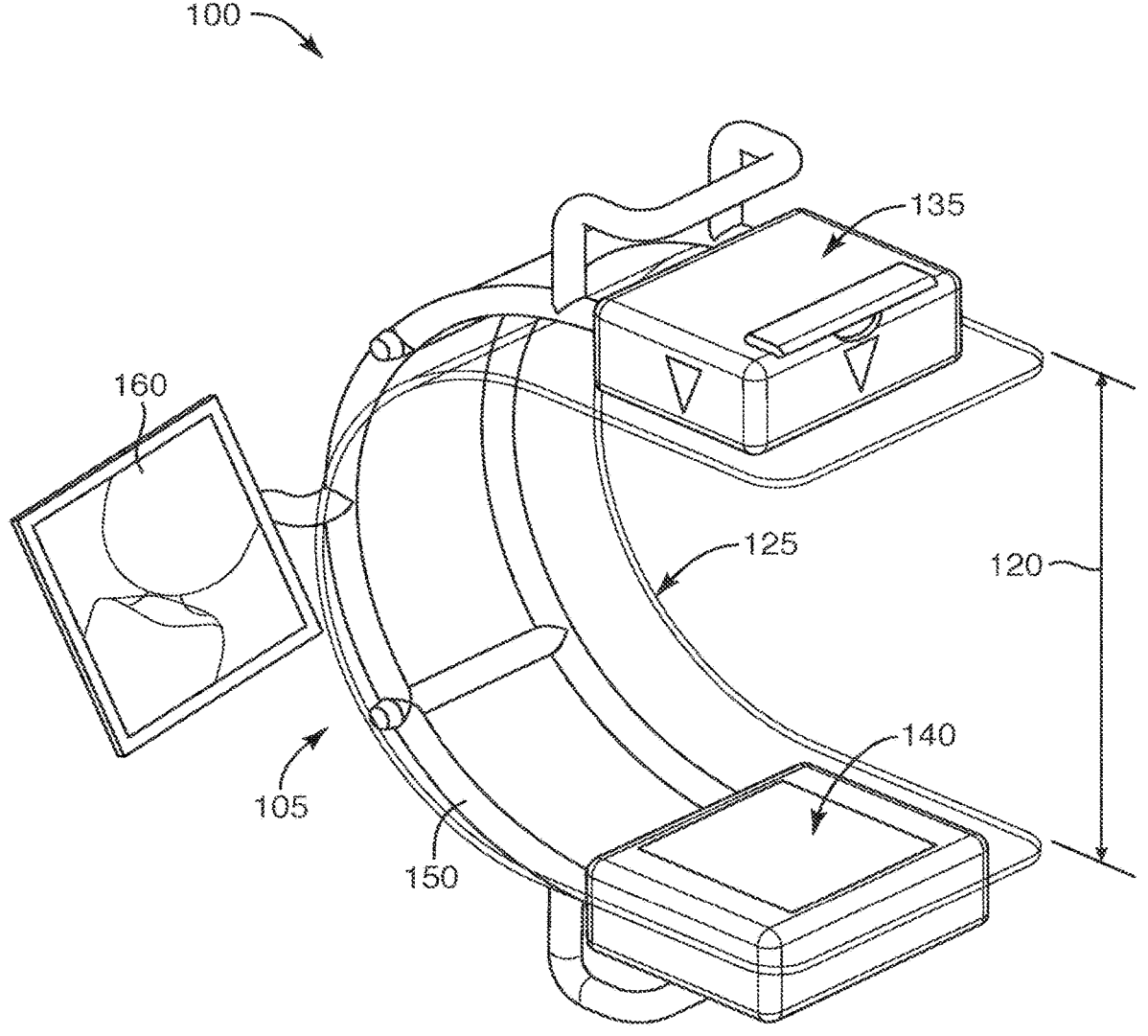
FIG. 1 shows a view of some embodiments of small, portable X-ray devices.

FIG. 1 shows some embodiments of small, portable X-ray devices 100 that can be used in the x-ray systems described herein. Generally, the portable X-ray devices 100 contain an imaging arm that allows the system to be used to take X-ray images of a portion of a patient's body or any other object capable of being analyzed by x-rays, including animals, industrial components such as electronic circuit boards, containers to be inspected, and/or passenger luggage. In some configurations, the imaging arm is substantially shaped like the letter "C" and is therefore referred to as a C-shaped support arm (or C-arm) 105. The C-arm has any size that can be held and operated by hand when in use, as seen in FIG. 1.

The C-arm 105 can contain any X-ray source 135 and X-ray detector 140 that allow the X-ray system 100 to take X-ray images. The X-ray source 135 can contain any source that generates and emits X-rays, including a standard stationary anode X-ray source, a micro-focus x-ray source, a rotating anode x-ray source, and/or a fluoroscopic X-ray source. And the X-ray detector 140 can contain any detector that detects X-rays, including an image intensifier, a CMOS camera and/or a digital flat panel detector. In some configurations, the detector can have a substantially square shape with a length ranging from about 13 cm to about 15 cm. In other configurations, the detector can have a substantially rectangular shape with the shorter dimension ranging from 12 cm to 16 cm, and the longer dimension ranging from 18 cm to 24 cm. The X-ray source 135 can be contained in a housing that can be configured in two parts with a first part enclosing the x-ray source 135 and a second, separate part enclosing the x-ray detector 140. In other configurations, however, the housing can be configured so that it is a single part that encloses both the X-ray source 135 and the X-ray detector 140.

In some configurations, the housing can also enclose a removable power source (such as a battery) and optionally a power supply. Thus, the power source and the power supply can be located internal to the housing and also to the x-ray device 100. The supporting electronics for the power source and the power supply, as well as the supporting electronics for an image display and for wireless data upload, can also be located internal to the housing. Thus, in these configurations, the x-ray device 100 does not contain an external power cord or data cable. Incorporating the power source (i.e., the battery), the power supply, and the supporting electronics all within the housing allows the size and the weight of the device to be reduced. With such a configuration, the power source can easily be replaced (or hot-swapped) and delivers 60 or more x-ray images using a single charge. Of course, if needed, the x-ray device can be configured so that it is alternately, or additionally, charged using external power from a power cord that is plugged into a wall outlet. In other configurations, multiple power supplies can be provided for the source, detector, and control electronics, any (or all) of which can be located either internal or external to the housing.

The X-ray device 100 also contains a frame 150 that has an open configuration. As shown in FIG. 1, an open configuration gives a number of easy gripping options for a user to carry and hold the frame 150 during transport, and optionally during operation of the x-ray device 100. In some embodiments, the frame 150 can be configured as a modular unit so different cross members (or length member or handles) can be used to replace the existing cross members (or length member or handles). Thus, the frame 150 provides the ability for a user (or operator) to grip and hold the X-ray device 100 during operation, a feature that is useful since other conventional C-arms can't be held in the hands while being operated because they do not have a suitable frame and because they are too heavy.

Figure 2:
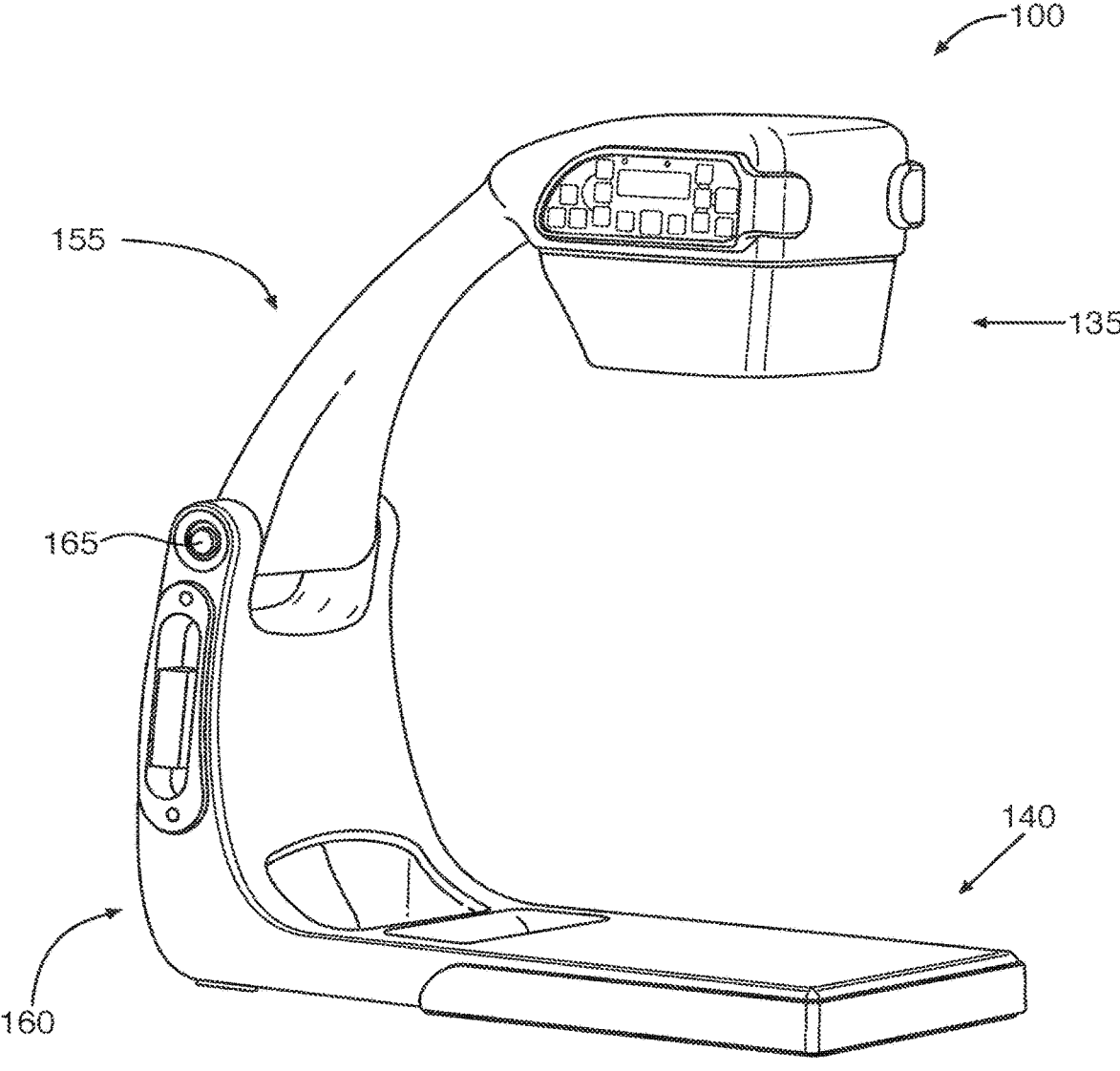
FIG. 2 shows another view of some embodiments of small, portable X-ray devices.

In other embodiments, the portable x-ray device has the configuration as illustrated in FIG. 2. In the embodiments of FIG. 2, the frame 150 has a first portion 155 that is part of the housing that also contains the x-ray source 135 and the associated electronics. The frame 150 also has a second portion 160 that is part of the housing that also contains the x-ray detector 140 and the associated electronics. The first portion 155 of the housing and the second portion 160 of the housing are connected using hinge 165. The bottom of the portable x-ray device can contain an opening 175.

The portable x-ray device 100 has several features not exhibited by other C-arm devices. First, it has the capability of wireless data transfer, thereby eliminating the need for any wired connections or data cables to the C-arm. Second, it is internally powered by a battery or internal power source and, therefore, more portable than other C-arm devices which require a power cable. Third, it is lighter that other C-arm devices. As a comparison, the portable x-ray C-arm devices 100 described herein can have a weight ranging from about 10 to about 25 pounds while other C-arm devices have a weight ranging from about 35 to about 375 pounds. In other embodiments, the portable x-ray C-arm devices 100 described herein can have a weight ranging from about 12 to about 18 pounds.

Figure 3A:
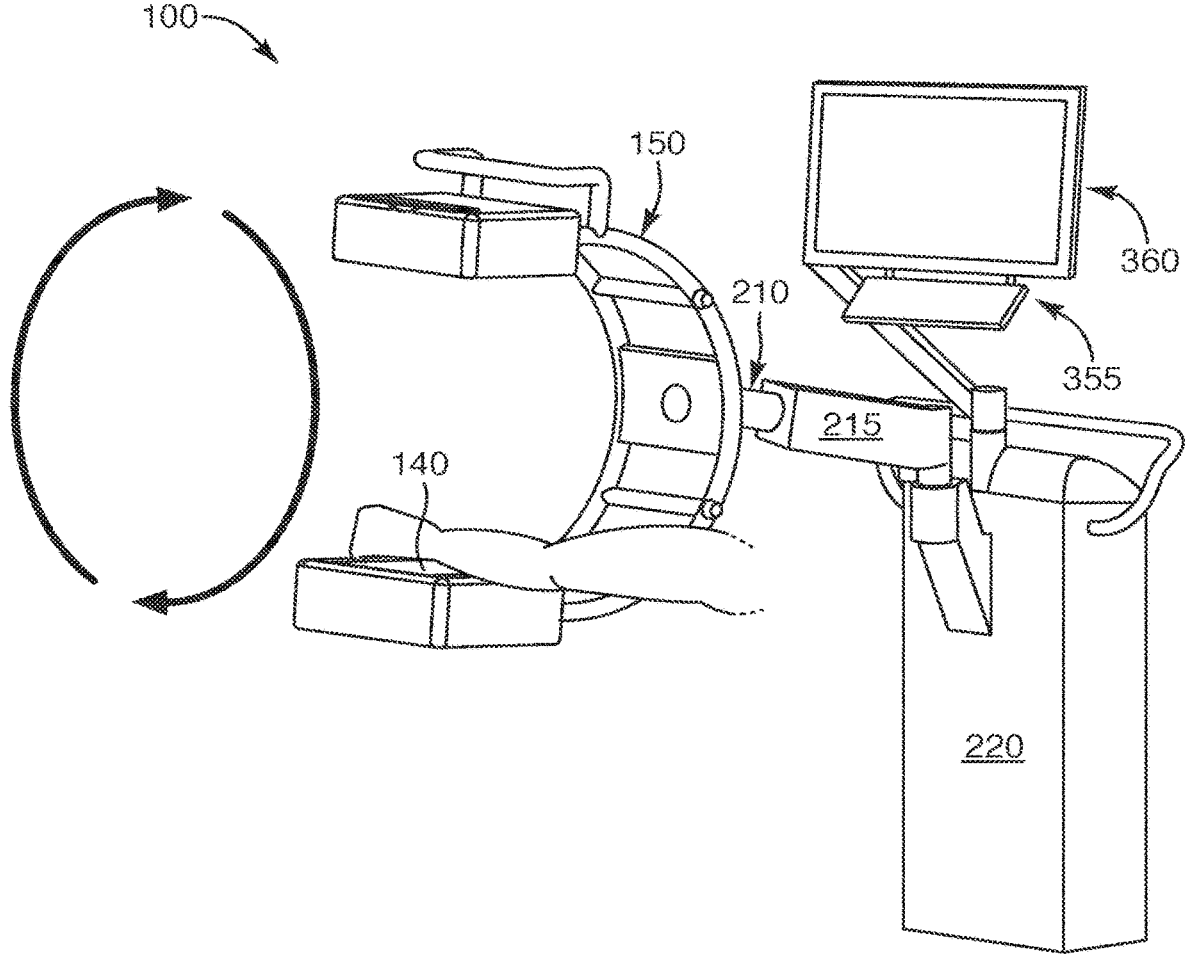
FIGS. 3A and 3B show a view of some embodiments of the range of motion of small, portable X-ray devices.
Figure 3B:
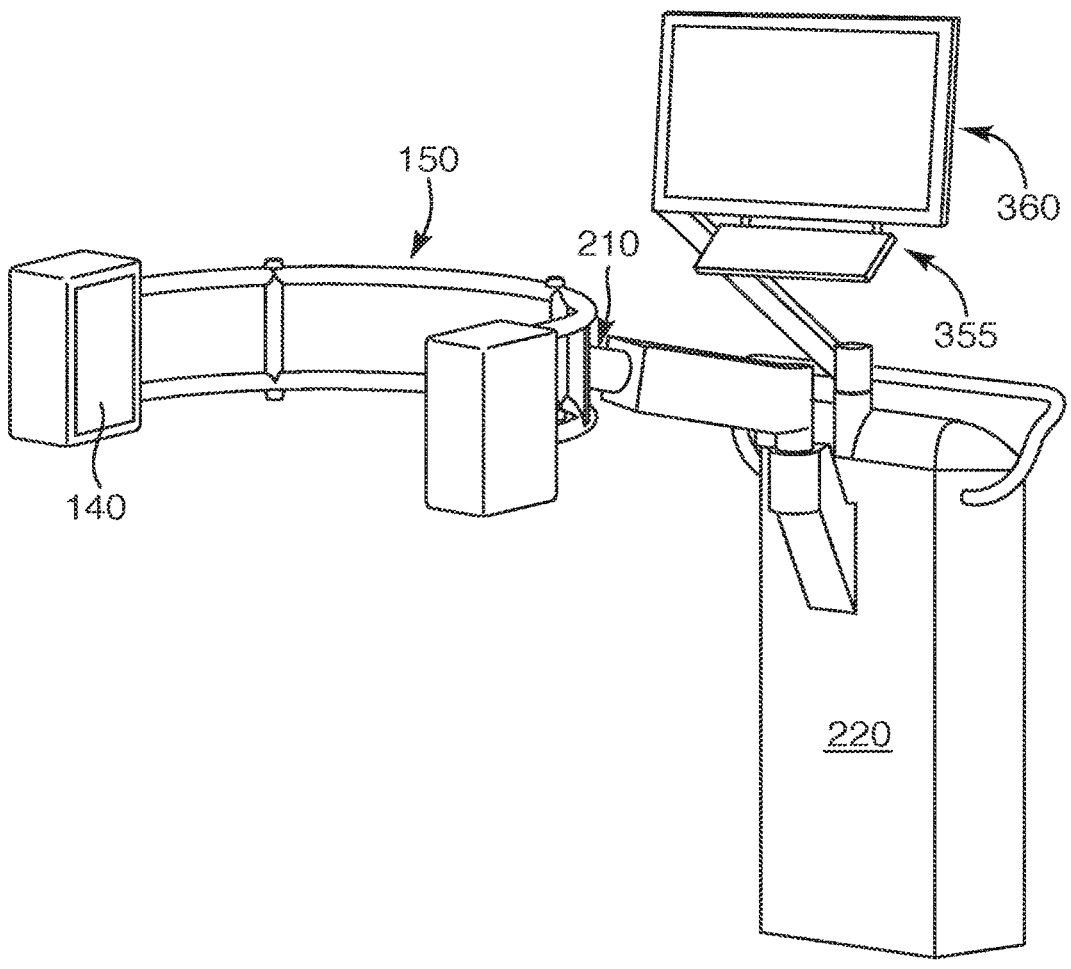

In some embodiments, the frame 150 can be connected to an external (or support) structure so that it can rotate around an object being analyzed, as shown in FIGS. 3A and 3B. In these embodiments, the connection between the frame 150 and the external structure contains a joint 210 that allows the following three functions. First, the joint 210 can be attached to the C-arm 105 and the support structure so that the C-arm 150, similar to other conventional C-arms, can rotate around the object (i.e., from the position in FIG. 3 to the position in FIG. 4) being analyzed (i.e., the arm of a patient). Second, the joint 210 allows the X-ray device to be quickly and easily attached (and detached) from the external structure. And third, the joint 210 allows the connection between the X-ray device 100 and the external structure to be located at any desired location of the frame (e.g., at 15, 30, 45, 60, 75, 90, 105, 120, 135, 150, and 165 degrees along the arc of the C-arm, or at any location therebetween). For example, as shown in FIG. 3A the joint 210 is connected to x-ray device 100 at about 90 degrees along the arc of the C-arm while in FIG. 3B the tri-joint 210 is connected to x-ray device 100 at about 60 degrees. Besides these motions, the C-arm 150 can slide along a sector bearing, or "nod" around the object, to capture the 2D images as shown in FIG. 4.

Figures 4, 5:
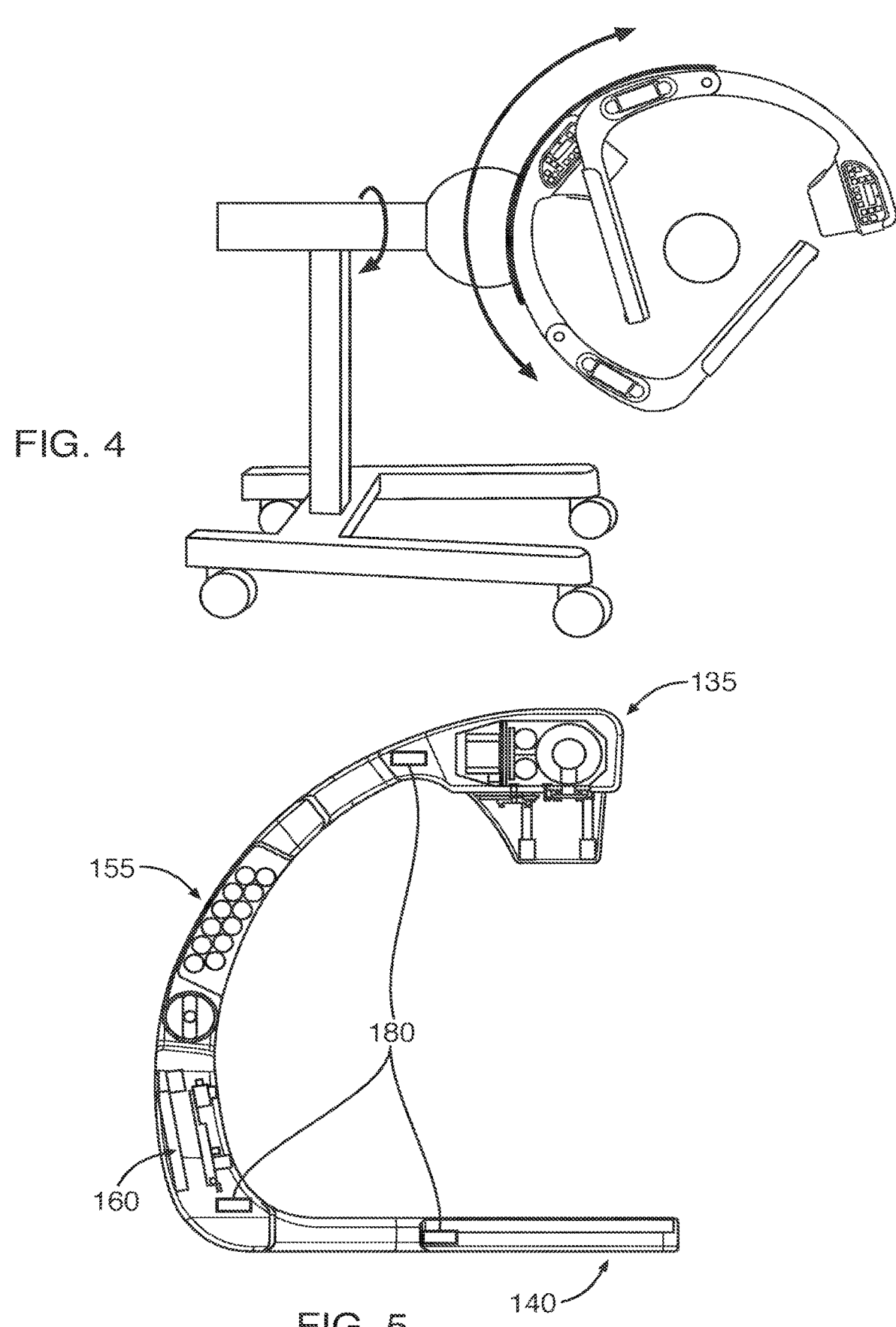
FIG. 4 shows another view of other embodiments of the range of motion of small, portable X-ray devices.
FIG. 5 shows another view of some embodiments of small, portable X-ray devices containing tracking devices.

FIGS. 3A, 3B, and 4 show some embodiments in which the joint 210 is attached at one end to the frame 150 of X-ray device 100 and at the other end to an extension 215 that extends from the external structure. In the embodiments shown in FIGS. 3A and 3B, the external structure comprises a supporting base 220 to which the extension 215 is connected. The support structure can also contain any other medical components and electronic components, as described herein, like the display 360 and the user interface 355 shown in these Figures.

In the configurations shown in FIGS. 3A, 3B, and 4, the x-ray system can include a motion-controlled stage or support arm. This stage may comprise mounting the C-arm device to a sector bearing spanning an angular range of approximately 200°, as depicted in FIGS. 3A, 3B, and 4. The C-arm can be positioned with the target area of the patient (a foot, knee, etc. . . . ) at the approximate center of rotation. The C-arm can then be scanned through this arc over the desired amount of time ranging from about 3 to about 10 seconds. In some embodiments, this time is approximately 5 seconds.

In some embodiments, the x-ray devices and systems can be configured similar to the C-arm device shown in FIG. 5. In these embodiments, the electronics can be modified for the special purpose of 3D imaging by including a tracking mechanism into the x-ray device. In some configurations, the tracking mechanism can be integrated into either the C-arm or other mechanical structure that positions the X-ray source and the X-ray detector relative to one another. In other configurations, the tracking mechanism can be external to the C-arm or other mechanical structure that positions the X-ray source and the X-ray detector relative to one another. In yet other configurations, the tracking mechanism can be located in any mechanical structure that supports the C-arm. The tracking mechanism can be configured to track and record the position and orientation of the x-ray system, including the x-ray source and/or detector for each 2D projection of the object taken along the image acquisition trajectory.

In some configurations, tracking devices 180, including MEMS inertial tracking devices, can be mounted in the C-arm as shown in FIG. 5 to provide geometric position information when each image frame acquired. These tracking devices can be mounted in at least 2 separate positions, one near the x-ray source and the other near the x-ray detector in order to provide the position information for both the x-ray source and detector. Depending on the type of tracking device used (whether or not the tracking devices can accurately track orientation as well as position), a third tracking device may need to be placed at a third location in the arm in order to determine the orientation of the components of the x-ray system for each 2D x-ray projection image taken during the scan. In other embodiments, the tracking devices can be included in other locations of the x-ray system, such as on more distal portions of the x-ray source and detector as well as further along the arm of the C-arm. Indeed, any number of tracking devices could be incorporated into the C-arm, provided that at least one tracking device is located near the source and one near the detector.

In some configurations, the tracking devices 180 depicted in FIG. 5 should meet certain accuracy requirements in order for the 3D reconstruction to be successful with the necessary resolution. As an example of the type of tracking device that could serve this purpose, MEMS tracking devices from a variety of vendors are available for a variety of purposes and can be used, but may not always deliver the needed resolution. A tracking device that can accurately and repeatably report the 3D position to within about 0.5 mm of the X, Y, and Z positions should be sufficient. Of course, with improvements in the computational speed of the graphical processor or other extremely high-speed computational device, it may be possible to relax this requirement and still achieve the desired 3D reconstruction performance. As well, it may also be possible to reduce the computational requirement by achieving better accuracy than the 0.5 mm requirement mentioned above. Therefore, an accuracy of about 1.0 mm, about 0.75 mm, about 0.5 mm, about 0.25 mm, or even about 0.1 mm may be practical and used in some embodiments. In other configurations, this accuracy can be any combination, sub-combination, or range of these amounts.

Tracking devices can also be used to know the orientation of the X-ray source and the detector for each image in the sequence as their location and orientation progressively changes from image to image from an initial starting position. Depending on the choice of the tracking device to be used, the orientation can be determined by comparing the position of at least three different tracking devices and calculating the relative orientation from image to image directly from the 3D information provided by each tracking device. This calculation is possible because the C-arm is a substantially rigid structure with a known configuration that can be relied upon to keep the relative position of the tracking devices constant to within a tolerance of about 0.25 mm, about 0.20 mm, about 0.1 mm, about 0.05 mm, about 0.01 mm or even less from image to image. In other configurations, this tolerance can be any combination, sub-combination, or range of these amounts.

In these embodiments, the tracking devices 180 can also provide orientation information as well as 3D position information. It is believed that an orientation accuracy on the order of about 0.5 degree of the solid angle will be sufficient during the 3D imaging process. Again, relaxing or tightening this tolerance should be possible and is believed to involve a trade-off between computing power, reconstruction time, and accuracy. Therefore, an orientation accuracy of less than about 2 degrees, about 1 degree, about 0.75 degrees, about 0.5 degrees, about 0.25 degrees, or about 0.1 degree of the solid angle is believed to be practical and functional in various embodiments. In other configurations, this orientation accuracy can be any combination, sub-combination, or range of these amounts.

As noted herein, the tracking devices can include MEMS inertial tracking devices. Other examples of tracking devices that can be used include accelerometers, light sensors, optical cameras, magnetic field sensors, and/or electromagnetics sensors. The types of light sensors that can be used include infrared sensors, ultraviolet sensors, and/or radio-frequency sensors.

Figure 11:
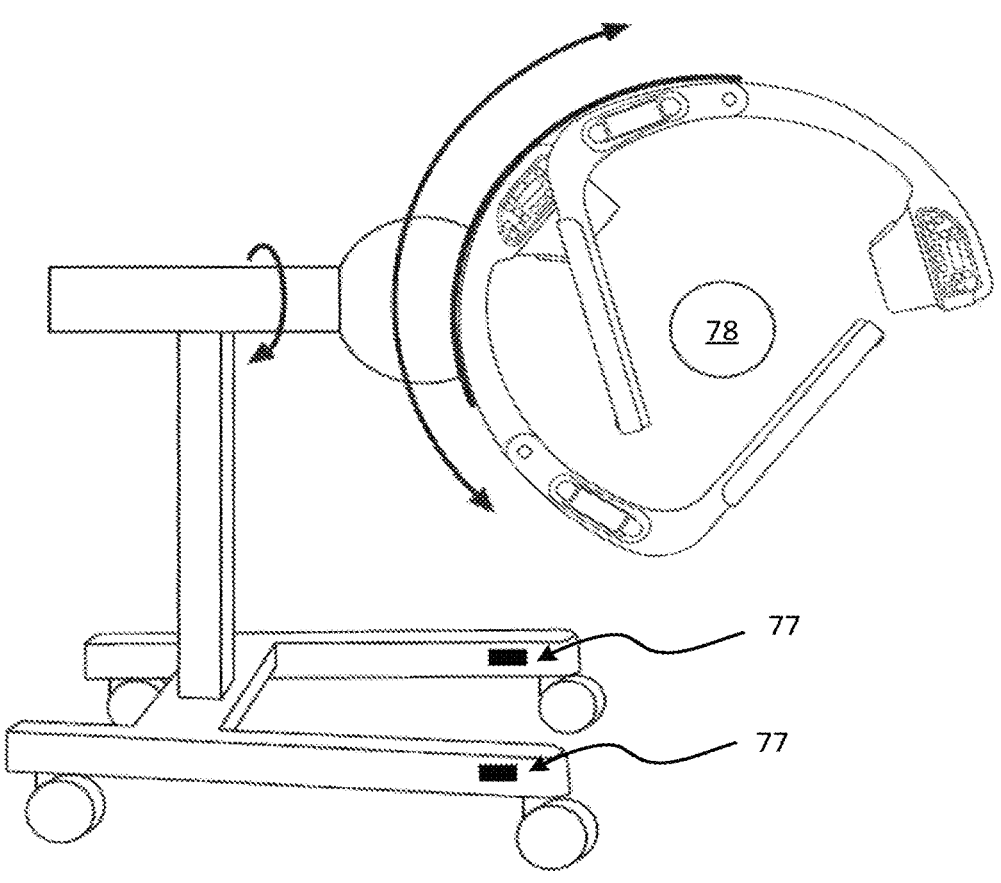
FIG. 11 shows some embodiments of the small, portable X-ray devices containing an external tracking device(s).

In other embodiments, the tracking mechanism can include a tracking device(s) that is not located in a position on the C-arm that positions the X-ray source and the X-ray detector relative to one another. These external tracking devices may be any of the tracking devices listed herein. One example of these external tracking devices is shown in FIG. 11 where external tracking devices 77 are located in the ends of the legs of the supporting structure holding the C-arm. Another example of these external devices are those that are not contained on the mechanical support structure shown in FIG. 11, such as tracking devices that could be located in the proximity of the objection being analyzed (object 78).

In other embodiments, the external tracking devices may include a fiducial marker or an arrangement of fiducial markers. A fiducial marker (or fiducial) is an object placed in the field of view of an imaging system that appears in the image produced, for use as a point of reference or a measure. It may be either something placed close to, into, or on the object to be imaged.

The accuracy of these 3D x-ray imaging systems can be improved using these fiducial markers. In order to reconstruct 3D images using tomosynthesis techniques or other mechanisms for assembling 3D images, it is important to know where the x-ray source is on a path in relation to the X-ray detector. While many of these paths are predetermined, small variances in patient location can result in minor deviations from the desired path on a frame-to-frame basis. These errors can be compound in a tomosynthesis process, resulting in a compounding loss of quality in a final 3D image assembled from the 2D X-ray images. In order to account for these small variances in detector position, the geometric location of the X-ray source can be independently calibrated with respect to the detector for each 2D X-ray image by using the fiducial marker(s).

In some configurations, the fiducial marker may comprise one or more small balls or spheres positioned somewhere in the field of view for each 2D X-ray projection image. This type of marker can be placed in such a way that each of the spheres is part of an arrangement of spheres, where the distances from one sphere to the next are known to a high degree of precision relative to the pixel size of the 2D images. A data file can then be developed that holds the locations of each object in the array, linking that to the X-ray source and detector combination, describing the locations of the spheres in the array.

As well, the fiducial marker(s) may be used with an external device coupled to the x-ray imaging device or by just utilizing a marker placed external to the x-ray device, such as a medical instrument (e.g., a catheter), or even near the object being analyzed such as a table where a patient is located. In other configurations, the array of fiducial markers can be incorporated into an object that is combined with—or held by—the housing containing the x-ray sensor/detector. Since the marker(s) will usually be located at the region of interest, this increases the accuracy of detection in this region, and thus improves the three dimensional reconstruction quality.

In some embodiments, an arrangement(s) of fiducial markers can be used. Specifically, the arrangement of markers can be positioned external to the C-arm. The arrangement of markers can be positioned such that each 2D image includes a projection of at least a portion of the arrangement of markers. The location of the source and/or detector of the x-ray device associated with the identified marker may be then determined while capturing the x-ray image.

In some embodiments, the arrangement(s) of markers can comprise an array of at least two fiducial markers. In such embodiments, each marker can be formed to have a cross-section in the shape of a circle, rectangle, rhombus, pentagon, hexagon, octagon, and/or polygon. The markers may be homogenous across or within the array, or the markers may differ across or within the array. A variety of marker shapes could be used at different points in the array.

The sizes of the markers can vary widely. They need to be small enough to have a significant number of markers in the image, but large enough that they are easy to detect. In some configurations, the sizes of the markers can vary across the array.

The x-ray systems described herein can be configured in some embodiments to be guided by a mechanical device positioned at the side of the operating room (OR) table (or other desired location) to gather the needed set of 2D projection images for the 3D reconstruction. In these embodiments, the purpose of the mechanical guidance mechanism is to simplify the task of the operator in appropriately capturing the needed 2D images by allowing the operator to move the x-ray systems on a mechanical guide or support by hand. This makes it easier for the operator in many cases since the weight of the system is born by the mechanical guide. It also makes it easier in that the operator does not have to move their arms and hands around the patient in ways that might be difficult or that might require the operator to position themselves awkwardly above the patient in order to cover the entire range of angles desired.

In other embodiments, the x-ray system can be guided by hand through the range of solid angles needed to reconstruct the desired 3D image. This would be straightforward in many instances, such as when a patient is standing upright and the x-ray system is moved around the patient's knee by hand, or similarly when a 3D image of an ankle or elbow is needed. Whether or not a mechanical guide is used would be determined by the physician based on the particular circumstances of each case.

The x-ray systems use high-powered, multi-threaded, multi-processor graphical processing units to render a 3D image quickly. In most applications, such as in the OR, it will be desirable to provide the reconstructed 3D image in less than two minutes, or even a minute. By adding additional processors or with improved software and other processing techniques, the 3D image can be rendered in less than about 45 seconds or perhaps even less than about 30 seconds. Of course, the rendering speed for a particular #D image will be determined by the acceptable trade-off between cost and rendering time.

The x-ray systems described herein also have a small footprint and a small size. Thus, instead of 3D images being obtained only with a special, large, and expensive CT apparatus used only when the costs can be justified, 3D images from these x-ray systems can be quickly and easily obtained. While the initial uses of the x-ray system will be to image specific parts of a patient (i.e., orthopedic surgeries and other similar applications), it can also include full-body imaging capability with x-ray sources that can provide the requisite x-ray energy and flux.

The x-ray systems described herein can be used for 3D imaging of patients similar to Computed Tomography (CT). CT is a common 3D imaging procedure used for diagnosis and treatment of fractures and for other surgical and medical procedures. Unfortunately, some current CT equipment doesn't meet the needs of many medical situations, including diagnostic requirements and surgical procedures, especially in situations that need a rapid response such as treating the victims of an accident or other emergency. This situation can occur because the CT equipment and facility is at a different location, or the difficulty and delay in conveying the patient to the CT facility makes obtaining 3D images impractical, especially when "before and after" images are desired to assess the results of a surgical procedure. This situation can also be caused by the expense of current CT equipment, because it is not cost effective to maintain CT equipment in every operating room or clinic.

Unlike some conventional CT systems, though, the x-ray systems described herein can be used for fast, accurate, low-cost, low-dose, and minimally-disruptive 3D imaging systems for use in and out of the operating room. In some embodiments, the x-ray systems described herein are referred to as Flexible 3D Computed Tomosynthesis (or F3CT) systems. The F3CT systems enable the 3D imaging mechanism to be brought to the patient, irradiate only the target area, provide immediate results, and enable the user or operator (i.e., surgeon or other medical personnel) to verify the 3D alignments and proper positioning of bone fractures, medical instruments, implants, or other objects or body parts needed to obtain the medically-desired results and to identify any defects or problems during the medical procedure, rather than afterward when it is not possible to correct the error or defect. The F3CT systems do not require the patient to be repositioned, or other equipment and personnel to be displaced during the procedure. Instead, these F3CT systems use a small, lightweight x-ray device which is easily stored and can be carried by hand (or moved on a small cart) to the side of the patient. The F3CT systems can be maneuvered around the affected limb, shoulder, or other body part in a prescribed manner (i.e., complete 360° coverage is not required) to capture the necessary 2D projections with the X-ray source and the detector following a path that covers a region of solid angle. The 3D reconstructed image can be presented within a short period of time (less than a minute or so) on a display screen.

Figure 6:
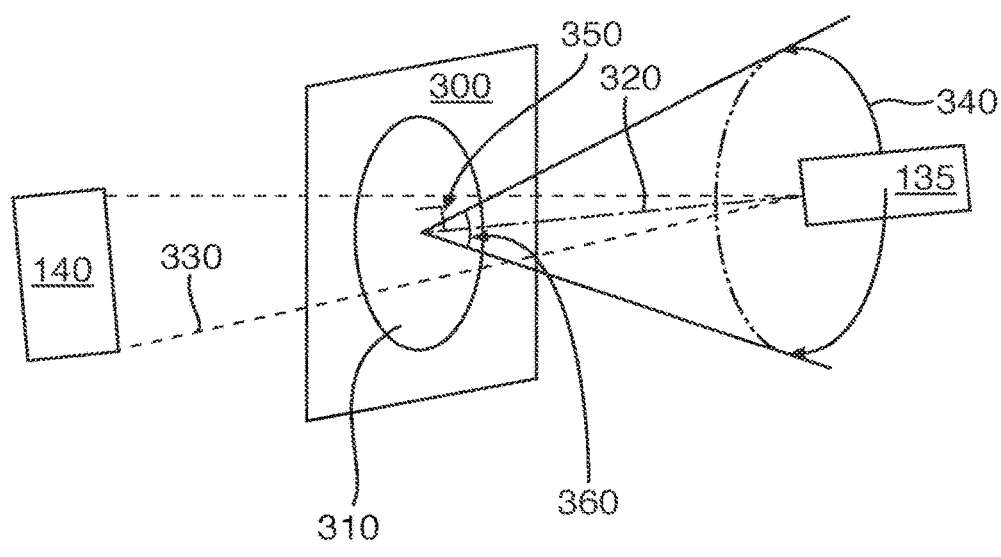
FIG. 6 illustrates an example of the planar arc acquisition path of some conventional CT imaging processes.

Some current inter-operative imaging systems use conventional fan-bean or cone beam CT processes. These systems collect x-ray projection images by rotating the x-ray source and the detector in a strictly constrained circular fashion around the object to be imaged, as shown in FIG. 6. As shown in this Figure, the source 135 and 140 are located on opposite sides of an object 300 that is being imaged. The source 135 and detector 140 are linked by a mechanical structure (such as a C-arm) that is not shown in FIG. 6. The x-rays 330 emanate from the source 135, impinge on a region 310 of the object 300, and then strike the detector 140. The motion of the source 135 is confined to a plane and describes a circle in that plane. As shown in FIG. 6, the arrows 340 are part of a circle that lies in a plane oblique to the page with a normal to the plane defined by axis 320 with the center of the circular arc located within the object 300. The process uses an axis of rotation 320 that is perpendicular to this planar arc 360. This collection process leads to the large toroidal shapes that are typical of conventional CT systems.

Figure 7:
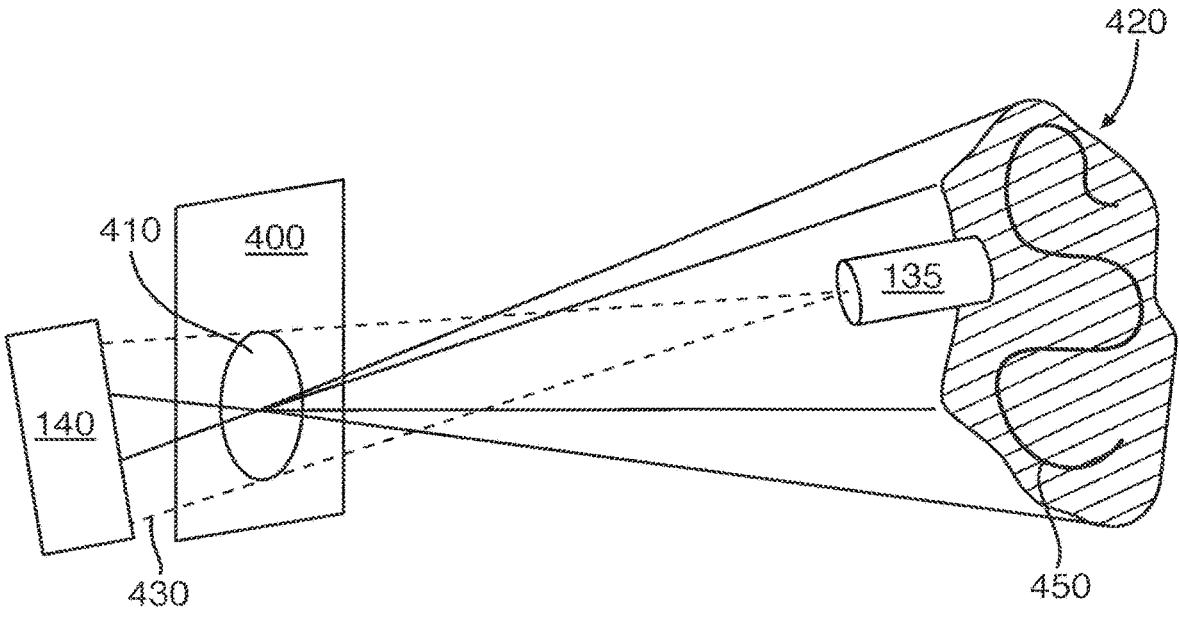
FIG. 7 illustrates some embodiments of a less-constrained or non-constrained acquisition path that covers a region of a solid angle.

Unlike these CT systems, the F3CT systems (and the x-ray systems described herein) can have a flexible data acquisition trajectory that cover or traverses a region of solid angle rather than following a substantially constant-radius arc that is confined to a particular plane. Such embodiments are illustrated in FIG. 7. As shown in this Figure, the source 135 and 140 are located on opposite sides of an object 400 that is being imaged. The source 135 and detector 140 are linked by a mechanical structure (such as a C-arm) that is not shown in FIG. 7. The x-rays 430 emanate from the source 135, impinge on a region 410 of the object 400, and then strike the detector 140. Rather than just being limited to rotating in a planar arc, though, the source 135 (and therefore also the detector 140 which is mechanically linked to the source 135) traverses or samples a region 420 of solid angle along an arbitrary path 450. There can be any number of paths that are possible and path 450 is illustrated in FIG. 7 for exemplary purposes only. Such an approach in these embodiments increases the challenge of image reconstruction since many data acquisition trajectories are possible and it can be difficult to precisely measure or track them. The F3CT systems accordingly use the internal or external tracking mechanisms described herein, as well as massive computing power now available in a graphical processing unit (GPU), to relax the mechanical constraints caused by the requirement to exactly know the scan geometry and to constrain it to a substantially constant-radius arc or series of arcs in one or more related substantially-parallel planes used in CT systems. In the F3CT systems, the constraints on the acquisition trajectory can be relaxed, thereby enabling an acquisition trajectory that covers or traverses a region of solid angle so that adequate 2D projection image data is obtained to provide a high-resolution reconstruction in all 3 dimensions, and computing power is used to solve the resulting complex reconstruction calculations.

The x-ray systems described herein can be configured as an ultra-compact C-arm (or other suitable mechanical configuration) that is hand-portable and/or hand-held when used. In these configurations, the weight should be minimized as much as possible, and can even be as light as about 15 lbs (7 kg). Of course, a variety of weights is possible, depending on the exact configuration of the C-arm, as long as the weight is not so much that it is impractical to be used as a hand-held device. Therefore, the weight might be about 25 lbs (12 kg), or about 20 lbs (9 Kg), or even perhaps as low as 10 lbs (4.5 Kg) in various configurations. The ultra-compact C-arm is suitable for use in any desired location, including the OR, surgical clinic, examination rooms, and other medical settings such as sports medicine, military field-hospital use, and emergency medicine settings such as at the scene of an accident or a natural disaster.

The x-ray systems described herein can contain a battery-operated x-ray imaging system with a 1500×1500 pixel, 100 μm resolution CMOS x-ray detector with a Cesium Iodide (CsI) scintillator. The use of a CsI scintillator provides for high sensitivity to x-rays and enables a lower dose to the patient. Of course, other detector technologies are possible, such as zinc selenide scintillators, CCD arrays, or other flat-panel detector array technologies that are known to those in the art.

In some configurations, the x-ray systems described herein can be designed for extremity imaging, with a source to detector distance of about 14 inches. Other configurations are possible within the constraints of the desired weight and size to allow for portability and operation by hand. Accordingly, the X-ray source to detector distance can vary anywhere from approximately 10 inches (25 cm) up to approximately 25 inches (64 cms), up to perhaps as much as about 30 inches (76 cm) but in some configurations the X-Source to X-ray detector distance be between about 12 inches (30 cm) to about 18 inches (46 cm). Of course, the detector size and the cone-angle or angular spread of the X-rays emitted by the x-ray source will need to be adjusted as this distance is changed so that the emitted X-rays fill the entire detector aperture, but do not extend appreciably beyond the edges of the detector.

In some embodiments, the detector size may be changed in order to match the size of the detector to the area illuminated by the X-ray source. However, it is not practical that the detector be too large because either this will required such large pixels in the detector that the resolution will be inadequate, or that there will be so many pixels in the 2D projections that the reconstruction of the 3D image will become impractical within the desired reconstruction times. In some configurations, a pixel size ranging from about 80 μm to about 200 μm will provide adequate resolution, and that a detector pixel dimension ranging from about 1000× 1000 pixels up to about 2500×2500 pixels will be appropriate. Other configurations would utilize a detector with a pixel dimension of about 99 μm and about 1500×1500 pixels.

The x-ray systems described herein can be controlled by an embedded processor running a version of Windows 10 (or other suitable operating system) that logs the image data, performs basic image processing, and correlates each 2D projection with the associated geometric (position and orientation) information obtained from the integrated geometric tracking system, such as those shown in FIG. 5. The combined 2D projection data can be transmitted using high-speed WiFi (or other suitable high-speed wireless data transmission means) to an external computer where additional image processing and 3D image reconstruction can be performed, and where 3D images can be displayed for use by the operator.

In some configurations, a wireless data transmission method can be used to convey the 2D projection data from the x-ray system to the external computer in order to eliminate data cables that would potentially get in the way or otherwise restrict the manipulation of the X-ray imaging system during a data acquisition scan. Similarly, the x-ray system can be battery powered in order to avoid power cables that could similarly restrict manipulation of the system.

The x-ray systems described herein can be configured to capture 2D projection images at a frame rate sufficient to capture all of the data required for reconstruction of the 3D image in a short period of time. An acceptable lower limit on the required framerate is believed to range from about 3 frames per second (fps) up to a rate of about 10 frames per second or more. The limitations on the image acquisition rate come from the possible WiFi data transmission rate, the practical detector data read-out rate, and the exposure or pulse repetition rate for the X-ray source. Currently, the data acquisition frame rate is primarily limited by the WiFi data transmission speed. As WiFi technology further improves, though, it is expected that practical image frame rates will climb to 20 fps or more and speeds up to and perhaps beyond 30 fps will be possible. At some point the speed at which the system can be guided by hand along a 2D projection acquisition path will become a limiting factor for the desirable frame rate because too many 2D projections that are geometrically too close to each other will not provide significant benefit in the 3D reconstruction, while exposing the patient to unnecessary radiation dose. For these, and other reasons, it is believed that the operating frame rate will always be between about 5 fps and about 20 fps, and in some embodiments might be about 10 fps.

In some embodiments, the size and resolution of the images can be increased while maintaining the necessary frame rate. These embodiments utilize an image size of about 1500×1500 pixels. Larger images are of interest, such as about 1700×1700 pixels, or about 2000×2000 pixels, or even up to about 3000×3000 pixels or more. It is also not necessary that the image remain square, so video images with dimensions of about 1500×2000 pixels, or about 2000× 3000 pixels or other dimensions are also possible. The technology used could be a CCD array coupled to a cesium iodide scintillation plate, or a CCD or CMOS array coupled to other x-ray scintillators such as sodium iodide, zinc selenide, calcium fluoride, and others.

Figure 8:
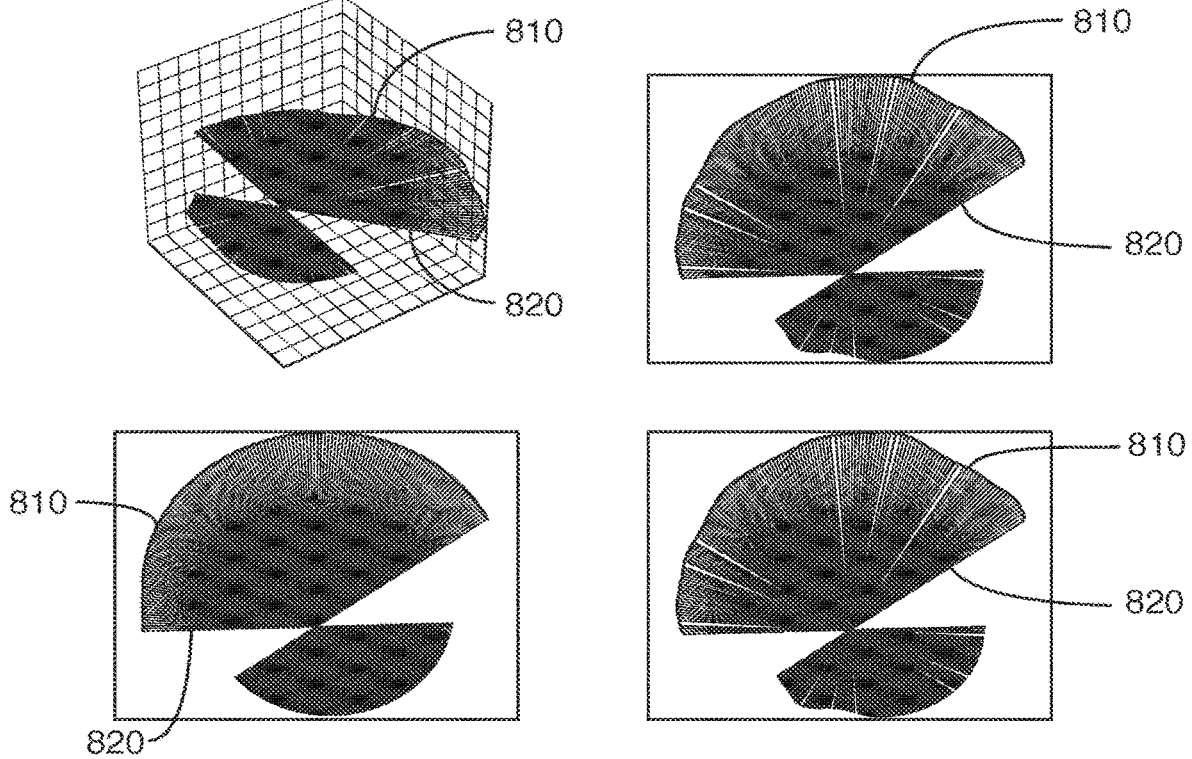
FIG. 8 shows a sample three-dimensional acquisition path (projected in two dimensions) of an x-ray system during a possible data scan.

As shown in FIG. 7 and described herein, the source and detector in the x-ray systems can be moved outside a planar acquisition path to scan or sample a region defined by a solid angle. FIG. 8 shows an exemplary 3D acquisition path, projected in two dimensions, of the x-ray systems during one possible data scan. The x-ray source of the C-arm follows the path 810 along the blue curve shown in the images on the right, and each red line 820 shows the path from the X-ray source to the detector for a particular image that can be captured. The upper left image in FIG. 8 shows a 3D view of ground truth, or completely accurate actual acquisition path. The upper right image in FIG. 8 shows a 2D projection of the ground truth acquisition path. The lower left image in Figure shows a 2D projection of the nominal (given) path. And the lower right image in FIG. 8 illustrates a 2D projection of the path as estimated at the beginning of the 3D reconstruction process.

Figure 9:
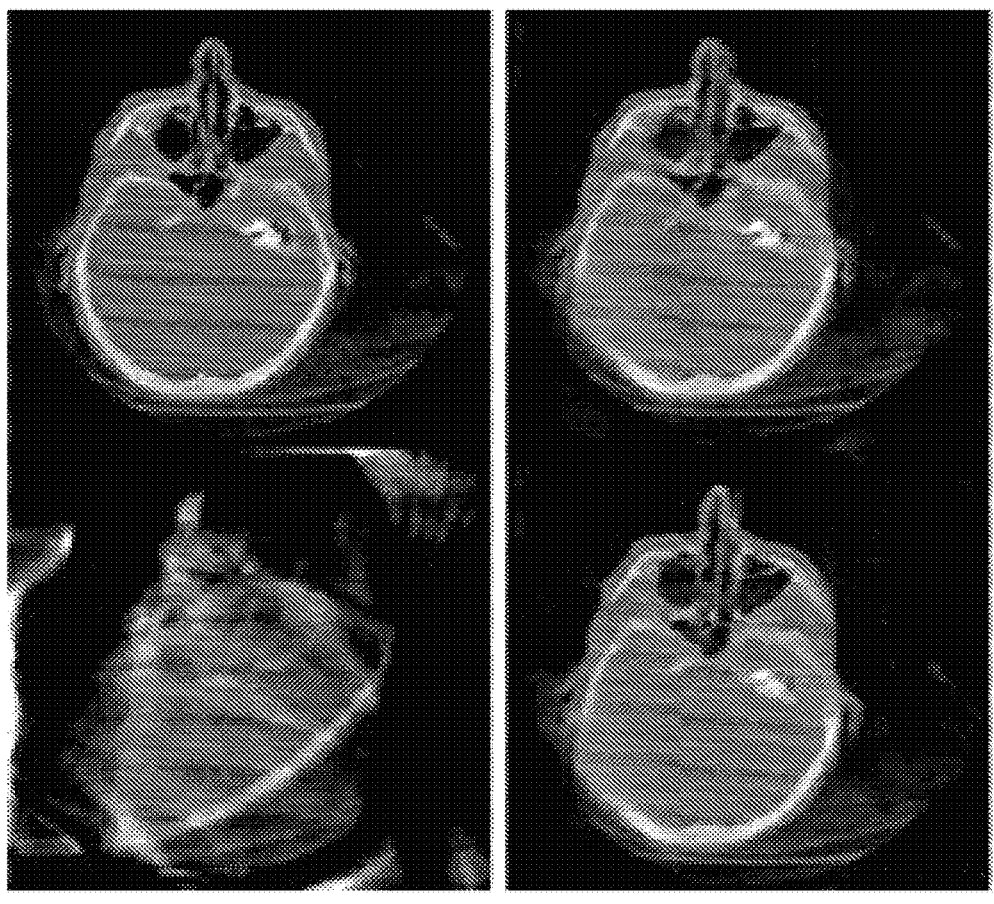
FIG. 9 shows an exemplary axial slice of a 3D reconstruction image obtained using tracking data.
Figure 10:
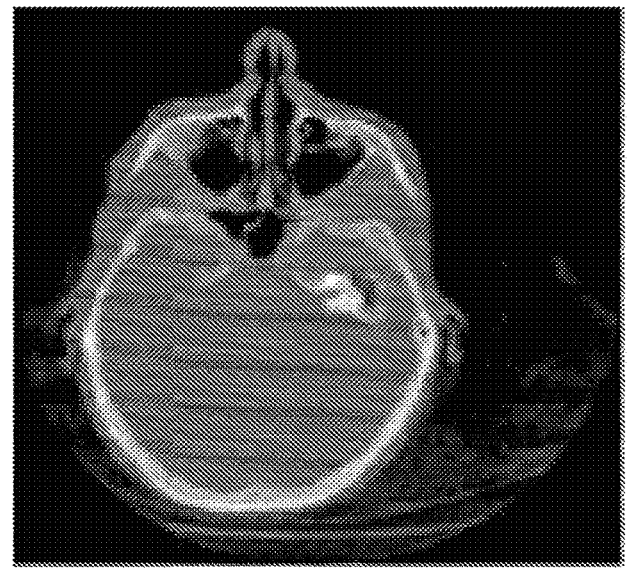
FIG. 10 shows an axial slice obtained using a CT image and a corresponding simulated 3D reconstructed image.
Figure 10:
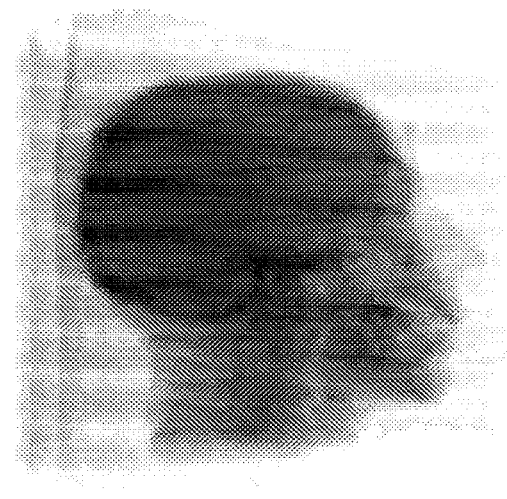

FIGS. 9 and 10 are examples of the 3D image reconstruction that can be obtained using the x-ray systems and methods described herein. FIG. 9 shows an axial slice of a 3D image reconstruction with tracking data. The upper left image in FIG. 9 shows a head CT dataset. The upper right image in FIG. 9 shows a reconstruction with ground truth parameters. The lower left image in FIG. 9 shows a reconstruction with nominal parameters. And the lower right image in FIG. 9 shows a reconstruction with geometry estimation. FIG. 10 shows an axial slice through the CT volume in the left image and a simulated Digitally Reconstructed 2D Radiograph (DRR) in the right image.

The x-ray systems described herein employ advanced tomosynthesis reconstruction algorithms that can be adapted and improved to reconstruct 3D images at a clinical level of performance despite the geometry uncertainty and errors that arise from a flexible acquisition trajectory using simple mechanical guidance or guidance by hand. Thus, once the 2-D image data is obtained, it can be processed to reconstruct the 3D image using software based on reconstruction algorithms that can account for uncertain geometry. Thus, the geometry of the acquisition scan can be irregular and uncertain and accordingly some conventional cone-beam reconstruction techniques will not work. While larger isocentric C-arms and fixed C-arms have much more consistent geometry, smaller mobile C-arms do not and are often moved by hand on an imprecise path. This scenario results in an uncertain geometry that has prompted work towards algorithms that can deal with these uncertainties or position and orientation errors.

Any 3D reconstruction technique can be used provided it can account for this uncertain geometry. For example, the Scientific Computing & Imaging Institute (SCII) at the University of Utah has proposed a method for 3D reconstruction in the presence of uncertain geometry. Instead of assuming a precise geometry based on expensive mechanical systems, this approach estimates the true geometry algorithmically while simultaneously estimating the 3D image. It is believed that algorithms such as that developed by SCII, or other algorithms that implement other means for estimating the true geometry in a 3D image reconstruction, while also meeting the requirements for speed and accuracy, will meet the requirements of the x-ray systems described herein.

The x-ray systems described herein, unlike some conventional approaches that employ a motion-controlled stage, capture the geometrical position of each 2D x-ray image as it is taken by the C-arm. The location in 3D space where each image is taken is not fixed, predetermined, or measured by the mechanical action of the motion-controlled stage and/or any electronics or positioning actuators that are part of the motion-control mechanism. Rather, it is measured by the internal tracking devices incorporated into the C-arm itself or the external tracking devices. This significantly reduces the cost, complexity, and the accuracy required of the stage because it is not determining the geometric position or causing any error in the geometric position of each image. The accuracy of, and any error in, each geometric position is attributable to the tracking devices.

Another improvement over these conventional approaches is that the motion of the stage, whether moved by hand or by a mechanism of some kind, is continuous. The short exposure time capability of the x-ray source (on the order of about 50 milliseconds or less, including about 25 ms, 10 ms, or even 5 ms or less) converts the challenge of mechanical stability and a stop-motion movement driven by a stepper motor or other similar device into a simple mechanical movement and a stop-motion image capture technique that is similar to taking a photo with a high shutter speed.

During operation of the x-ray systems described herein, there is a trade-off between the rate of motion of the C-arm during a scan and the need to keep the patient motionless during the scan. A high rate of motion will lead to a faster scan time, thus reducing the time during which the patient must remain substantially motionless. However, if the rate of motion is too quick, the resolution of the image will be impacted because of excessive motion of the x-ray source and the detector during the exposure time for each frame. Even if this exposure time is as short as 20 milliseconds, a high rate of motion will result in the detector or the x-ray source, or both, moving more than 100 microns or more during the exposure. This will introduce motion blur into the 2D image data and therefore may adversely affect the final rendered 3D image.

The imaging scan should also be completed in a total time frame that is short enough with respect to the ability of the patient to remain motionless. If the patient is anesthetized, than a scan that is completed in about 20 seconds, or about 30 seconds, or even about 45 or about 60 seconds may be acceptable. In other situations where the patient is conscious, a scan time of about 5 seconds, about 10 seconds, or perhaps about 15 seconds is necessary. With proper tomosynthesis calculation techniques, some small amount of patient motion can be accounted for, so a time of about 10 or about 15 seconds is probably acceptable, but for optimum image resolution the scan should be completed as quickly as possible in light of the trade-off between the rate of motion and the total scan time.

One method to determine the time in which a scan can be completed is to consider the effects of the motion of the x-ray source and detector upon the image resolution. If, for the sake of illustration, the distance from the x-ray source to the detector is about 15 inches (38 cm), and the object to be imaged is located half-way between the source and the detector. The motion of both the detector and the source between two consecutive image frames can be described as an arc around the object with a radius of 7.5 inches (19 cm). In order to avoid an effective loss of resolution on the detector due to motion during the acquisition of an image, the displacement of the detector during the image acquisition need not exceed the dimension of a small number of pixels in the direction of motion. In some embodiments, a limitation of 3 pixels or less can be used. To illustrate further, if the arc of rotation for the C-arm covers 120 degrees, and this arc is scanned within an interval of 20 seconds, the angular rate of motion would be 6 degrees per second. At a radius of 19 cm, this would be equivalent to the detector and the source both moving at a rate of 1.99 cm per second. If the detector pixel size is 100 μm, then the detector could be allowed to move by a maximum amount of approximately 300 μm during an image acquisition. Of course, if the detector motion during an image acquisition can be limited to 2 pixels or less, which would correspond to a maximum motion of approximately 200 μm, this would give better results. Given such a scenario, this would mean that each image should be acquired in a time of about 15 milliseconds.

This exemplary configuration is believed to be a practical exposure time for an image, though for a given x-ray source (and the associated x-ray flux) and a given x-ray detector (and the associated x-ray detection sensitivity), other exposure times may be used. In general, it is believed that a time of 25 milliseconds or less is preferable for a number of reasons, including the issues of patient motion as well as motion of the x-ray source and detector, therefore a time of 25 milliseconds, or 20 milliseconds, or 15 milliseconds, or perhaps even as little as 10 milliseconds or 5 milliseconds for an exposure may be preferred, depending on the detailed design of the system and the 3D imaging application. In other configurations, this time can be any combination, sub-combination, or range of these amounts.

When scanning in the region of the solid angle, C-arm is first scanned through the initial arc described above that lies in a single plane, as illustrated in FIG. 6. Then the sector bearing for the C-arm can then be rotated or shifted through an angle perpendicular to the sector arc and the C-arm would be scanned again. This angle could be optimized for the application and procedure, and may prove to be different for different imaging requirements. Thus, the total acquisition path would sample a region of the solid angle, as shown in FIG. 7 but with a different path than the arbitrary path shown in FIG. 7. A scan angle of about 10 degrees, about 20 degrees, about 30 degrees, about 40 degrees, about 50 degrees, about 60 degrees, about 70 degrees, about 80 degrees, about 90 degrees, about 100 degrees, about 110 degrees, and even 120 degrees or more could be used. In other embodiments, this path can be any combination, sub-combination, or range of these amounts. Of course, a larger angle will sample a larger region of solid angle so it is desirable to use as large a scan angle as practical. In some configurations, the angle used can be any combination, sub-combination, or range of these amounts. If necessary for the 3D reconstruction, the stage could be shifted to obtain a third (fourth, fifth, or even more) data scan. Shifting the stage and taking multiple scans will provide much higher z-axis resolution in the reconstructed 3D images. The entire scanning process can be completed in about 20 to about 30 seconds, or even about 10 seconds or less depending on the time between the scans and the rate of motion of the system.

In some embodiments, the stage of the system can be mounted on a lightweight (approximately 100 lbs) hand-mobile cart that would be moved into position at the side of the operating table when needed. It could take around 30 seconds (or less) to position the stage and C-arm appropriately with respect to the target area of the patient's body and initiate the scan. The entire process of moving the stage into place, positioning the system, gathering the data, and removing the stage could be completed within about 3 minutes, about 2.5 minutes, about 2 minutes, about 90 seconds, or even about 60 seconds by a trained surgical team. In other embodiments, this time can be any combination, sub-combination, or range of these amounts.

In some embodiments, the x-ray systems operate while being mounted on a mechanical device that guides the source and the detector as they trace a series of arcs that together would generally define a portion of a spherical surface, or in other words, a region of solid angle. This same type of motion or acquisition path for the system could also be used where the system is hand-held. However, it is not necessary in these embodiments that the system travel in a series of regular arcs of constant radius, as would easily be done with the mechanical device as described. The goal, in both the hand-held and the mounted configurations, is to obtain a sufficient number of 2D projection images to provide the data adequate for a reconstructed 3D image.

Especially in the hand-held configurations, but also true in the mounted configurations, it is not required that the radius (or distance of the X-source or detector from the object) of the region of solid angle covered during the acquisition scan be held constant, nor is it required that the path through the region of solid angle be a series of arcs. The path described by the X-ray source, for example, can be samples or segments of the region of solid angle, may be similar to a helix, or a spiral, or have the shape for the letter S, or may follow any other path as it covers the required region of the solid angle. Sufficient 2D projection images need to be obtained with sufficient differences in their solid angle orientation so that the 2D projection data contained in the set of images provides good and sufficient information on the 3D structure of the object to enable a successful reconstruction.

Thus, the x-ray systems simplify the mechanical motions required in capturing a 3D x-ray image, eliminate the mechanical constraints and issues entirely if the 3D scan is performed in a hand-held manner, and take advantage of the capability and performance of modern electronics, graphical processing systems and other high-speed data processors, along with advances in x-ray sources and digital x-ray detectors to obtain the necessary geometric position (and orientation) information and to implement the mathematical algorithms that can reconstruct a 3D image from the more complex and less exact geometric data set that will be produced in an scan.

The x-ray systems, devices, and methods described herein would be useful in analyzing and treating bone fractures. Among all types of non-fatal injuries, bone fractures are the leading cause of missed work days with a median of 30 days missed per fracture. Fractures, of all types, cause more than 70% of all hospital charges for musculoskeletal injuries in the US. Clearly, bone fractures are a common injury and have a significant impact on the typical patient. While data on what percentage of these fracture injuries currently require 3D imaging during treatment is difficult to find, conversations with orthopedic surgeons indicate that a quick, low-impact, easy-to-use 3D imaging system would be widely used in treating fracture injuries in order to avoid misalignments and positioning defects that are often difficult to detect with just 2D x-ray images.

During surgery, with only 2D images immediately available except in rare instances, guesswork is often required in positioning the bones, bone fragments, and joint surfaces involved in an injury or a corrective procedure. Often, the surgical repair that was perceived as fully corrected during the operation will demonstrate defects and changes in the postoperative x-rays from what was perceived in the OR and from the desired outcome. These defects and changes are, in large part, attributable to the inability of conventional 2D X-ray image to fully convey 3D information to the physician.

Conventionally, 3D images are often obtained using a Cone-beam or a Fan-beam X-ray source in which the x-ray source and detector are configured to move in tandem around the subject in a planar arc, as shown in FIG. 6 and described above, to obtain the desired projection images. The X-ray source and detector complete 360 degrees of rotation describing circles in a two-dimensional plane around the subject for the best reconstruction results with the best resolution for the reconstructed image slice that lies in that same plane. However, in many instances, 360 degrees of rotation is not possible for mechanical or other reasons of practicality. Whatever the extent of rotation around the circle in a two-dimensional plane, the resulting set of 2D projection images will not provide detailed information on the three-dimensional structure of the object that lays outside of that two-dimensional plane, because projection views of the object that lie only in a plane cannot provide information on details located outside of the plane. Thus, some conventional CT 3D images are often displayed as slices, and CT systems are configured so that the X-ray source and detector follow a helical path as they rotate around the subject.

There are other known methods for obtaining 2D projections, some of which are described in U.S. Pat. Nos. 9,014, 328, 7,333,588, 9,442,083, and 5,625,661. In these methods, a primary concern is to reduce the patient radiation dose by more effectively using the data provided by each 2D image projection, and to be able to obtain more accurate or reliable 3D reconstructed images of the object, or the region in the patient's body that is of interest.

Despite the advances in 3D X-ray image generation described in these patents, they so not described an inexpensive, easy-to-use, 3D imaging system and method that enables the 3D imaging device to be sufficiently mobile to be brought to the patient rather than requiring the patient to go to the machine, that does not require dedicated facilities and operators or expensive image display capability, that makes effective use of the data obtained from the radiation dose delivered to the patient, and that can provide high-resolution images in X, Y, and Z over a subject volume large enough to be useful for orthopedics or other medical applications, while sampling a relatively small geometric solid angle rather than just a portion of an arc in a plane. The devices, systems, and methods described herein improve over these, and other existing practices and devices, and incorporate unique features and capabilities to enable the reconstruction of 3D images where the set of two-dimensional x-ray images are not constrained in their geometrical configuration or geometrical relationship to an arc lying in a plane. Instead, they enable the use of an arbitrary or flexible geometrical path that traverses a region of solid angle for the x-ray source and detector during the acquisition of the images. They also reduce, or even eliminate, the need for complex and expensive mechanical systems that guide and tightly control the motion of the x-ray source and detector during acquisition of the set of 2D x-ray projection images. This significant advance in the technology of 3D X-ray imaging in the devices, systems, and methods described herein will also reduce the patient dose and the over-all expense and difficulty in obtaining and using 3D images in medical practice, such as in orthopedics. The capability to reconstruct 3D images for a more flexible or generalized geometrical situation enabled by the devices, systems, and methods described herein greatly increases the applicability and ease-of-use of 3D x-ray images.

To obtain these features, the x-ray systems described herein contain an arm (i.e., a c-arm) configured to be moved by hand around an object to be imaged, a light weight, bright, low power x-ray source attached to the arm, x-ray detectors synchronized to move with the x-ray source to capture multiple 2D projection images, a tracking mechanism to accurately record the location and orientation in three-dimensions of the x-ray source and detector at the moment each of the 2D images is captured, and an image processor or computer configured to accept the multiple, 2D images with a generalized, non-pre-determined or "fixed" geometry and use a reconstruction algorithm to construct a three-dimensional image of the object. Such a configurations allow creation of a 3D image of an object where the acquisition scans of the object are irregular, meaning the physical path in 3-dimensional space followed by the x-ray source and detector to obtain the series of 2D projection images, and the relative geometry of each of the 2D images is much less constrained than some conventional technologies for reconstructing 3D X-ray images. This does not mean that the geometry of the x-ray source and detector are not known, because the tracking mechanism provides complete and adequate information on the location and geometric orientation of the x-ray source and detector for each x-ray image relative to the other 2D projections, as well as relative to the subject being imaged. What is unknown or not known before the x-ray image scan is made is the exact location and orientation at which each 2D X-ray image will be captured. This is a departure from some conventional methods where the geometric location in 3D space at which each 2D X-ray image will be captured is known and pre-determined to a high degree of accuracy by the complex, carefully-designed, and expensive mechanical and electronic systems that control the position and motion of the X-ray source and detector during the X-ray image acquisition scan. Further, the x-ray devices described herein can be much lighter, more maneuverable, and much less expensive because the tracking mechanism, combined with the processor and algorithm, enables the generation of 3D images without knowing the precise geometry of each 2D projection image to a high degree of accuracy.

The x-ray systems, devices, and methods described herein can contain several modifications. In some modifications, multiple x-ray sources and/or multiple detectors can be used. In other modifications, collimators for the source or collimated detectors can be used. The imaging systems can also be modified to contain one or more position calibration mechanisms with a combination of technologies or other features. It is even possible that a position calibration mechanism can be used that will require only one device to be integrated into the X-ray system structure, as long as it provides the requisite position and orientation information in three-dimensional space.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. An imaging system, comprising:
an arm configured to move around an object to be imaged;
an x-ray source configured to move around the object without being constrained to a pre-determined path;
an x-ray detector configured to move in a path complimentary to the x-ray source and capture multiple two dimensional (2D) images;
tracking devices located external to the arm for capturing the position of the x-ray source and detector when each 2D image is captured; and
a processor configured to construct a three dimensional (3D) image from the multiple 2D images using a reconstruction algorithm.

2. The system of claim 1, wherein the tracking devices are located within the arm near the x-ray source and x-ray detector.

3. The system of claim 2, wherein an additional tracking device is integrated into the arm in a location other than near the x-ray source an x-ray detector.

4. The system of claim 1, wherein the tracking devices comprise a fiducial marker.

5. The system of claim 4, wherein the tracking devices comprise an array of fiducial markers.

6. The system of claim 1, wherein the movement of the x-ray source and x-ray detector are not in a planar arc.

7. The system of claim 6, wherein the movement of the x-ray source and x-ray detector are in a region of a solid angle outside of the planar arc.

8. An imaging system, comprising:
a C-arm configured to move around an object to be imaged;
an x-ray source in a first portion of the C-arm and configured to move around the object without being constrained to a pre-determined path;
an x-ray detector in an opposing portion of the C-arm and configured to move complimentary to the x-ray source to capture multiple two dimensional (2D) images;
tracking devices for capturing the position of the x-ray source and detector when each 2D image is captured; and
a processor configured to construct a three dimensional (3D) image from the multiple 2D images using a reconstruction algorithm.

9. The system of claim 8, wherein the tracking devices are located within the arm near the x-ray source and x-ray detector.

10. The system of claim 9, wherein an additional tracking device is integrated into the arm in a location other than near the x-ray source and x-ray detector.

11. The system of claim 8, wherein the tracking devices are located external to the arm.

12. The system of claim 11, wherein the tracking devices comprise a fiducial marker.

13. The system of claim 12, wherein the tracking devices comprise an array of fiducial markers.

14. The system of claim 8, wherein the movement of the x-ray source and x-ray detector are not in a planar arc.

15. The system of claim 14, wherein the movement of the x-ray source and x-ray detector are in a region of a solid angle outside of the planar arc.

16. A method for imaging an object, comprising:
providing an x-ray source and an x-ray detector on opposing sides of a C-arm;
moving the x-ray detector and the x-ray source in a complimentary path around the object without being constrained to a pre-determined path to capture multiple two dimensional (2D) images;

tracking the position of the x-ray source and detector when each 2D image is captured; and forming a three-dimensional (3D) image of the object from the multiple 2D images using reconstruction algorithm.

17. The method of claim 16, wherein tracking devices are located external to the C-arm to track the positions of the x-ray source and x-ray detector.

18. The method of claim 17, wherein the external tracking devices comprise a fiducial marker.

19. The method of claim 18, wherein the external tracking devices comprise an array of fiducial markers.

20. The method of claim 16, wherein the movement of the x-ray source and x-ray detector are not in a planar arc.

21. The method of claim 16, wherein the movement of the x-ray source and x-ray detector are in a region of a solid angle outside of the planar arc.

* * * * *